(12) United States Patent
Meriaux et al.

(10) Patent No.: US 9,829,420 B2
(45) Date of Patent: Nov. 28, 2017

(54) APPARATUS AND METHOD FOR OPTIMIZING A TEST BED THAT IS UTILIZED FOR TESTING LOW CYCLE AND HIGH-CYCLE FATIGUE INCLUDING MODIFYING A SUPPORT

(71) Applicant: SNECMA, Paris (FR)

(72) Inventors: Jean Vincent Manuel Meriaux, Moissy-Cramayel (FR); Guillaume Puech, Moissy-Cramayel (FR); Juan-Antonio Ruiz-Sabariego, Moissy-Cramayel (FR); Nathalie Serres, Moissy-Cramayel (FR)

(73) Assignee: SNECMA, Paris (FR)

( * ) Notice: Subject to any disclaimer, the term of this patent is extended or adjusted under 35 U.S.C. 154(b) by 61 days.

(21) Appl. No.: 14/890,498

(22) PCT Filed: May 15, 2014

(86) PCT No.: PCT/FR2014/051124
§ 371 (c)(1),
(2) Date: Nov. 11, 2015

(87) PCT Pub. No.: WO2014/184494
PCT Pub. Date: Nov. 20, 2014

(65) Prior Publication Data
US 2016/0109344 A1    Apr. 21, 2016

(30) Foreign Application Priority Data
May 17, 2013    (FR) .................................. 13 54436

(51) Int. Cl.
*G01N 3/32*    (2006.01)
*G01N 3/24*    (2006.01)
(Continued)

(52) U.S. Cl.
CPC ................. *G01N 3/32* (2013.01); *G01N 3/24* (2013.01); *F01D 5/3007* (2013.01);
(Continued)

(58) Field of Classification Search
CPC ..... G01L 9/0054; G01L 19/141; G01L 15/00; G01L 19/148; G01L 9/0073;
(Continued)

(56) References Cited

U.S. PATENT DOCUMENTS 6,250,166 B1    6/2001   Dingwell
6,718,833 B2    4/2004   Xie
(Continued)

FOREIGN PATENT DOCUMENTS

| EP | 2 241 872 A2 | 10/2010 |
|---|---|---|
| FR | 2 927 997 A1 | 8/2009 |
| WO | 03/021233 A1 | 3/2003 |

OTHER PUBLICATIONS

International Search Report dated Jul. 3, 2014, issued in corresponding International Application No. PCT/FR2014/051124, filed May 15, 2014, 3 pages.
(Continued)

*Primary Examiner* — Lisa Caputo
*Assistant Examiner* — Brandi Hopkins
(74) *Attorney, Agent, or Firm* — Christensen O'Connor Johnson Kindness PLLC

(57) ABSTRACT

A method for optimizing a low cycle and optionally high-cycle fatigue test rig includes selecting variable geometric parameters of the support member and/or of the workpiece of the rig, in addition to ranges of variation of these parameters, selecting at least one aim or design objective to be achieved, a variation in the values of at least a part of the abovementioned parameters having an influence on this aim or design objective, and testing one or a plurality of the
(Continued)

values of the abovementioned parameters, in the respective ranges of same, and determining those values that make it possible to achieve the aim or design objection. With those values, the method including producing or modifying a support member and/or a workpiece on the basis of the optimized parameters.

13 Claims, 4 Drawing Sheets

(51) Int. Cl.
F01D 5/30 (2006.01)
G01N 3/08 (2006.01)
F01D 25/28 (2006.01)

(52) U.S. Cl.
CPC .............. *F01D 25/285* (2013.01); *G01N 3/08* (2013.01); *G01N 2203/0073* (2013.01); *G01N 2203/0246* (2013.01); *G01N 2203/0298* (2013.01)

(58) Field of Classification Search
CPC .......... B81B 7/0058; B81B 2201/0264; B81B 2207/015; B81B 2201/025; B81B 2207/12; B81B 7/0061; H01L 2224/48091; H01L 2224/48247; H01L 2924/1815; H01L 2924/00014; H01L 2224/48465; H01L 2924/00; H01L 2924/1461; H01L 29/84; H01L 2224/48137; H01L 2224/45144; H01L 2924/181; H01L 2924/3025; H01L 2924/15747; H01L 2924/00012; B81C 2203/0154; B81C 1/00309; Y10T 29/49126
USPC .......................... 73/721, 715–717, 727, 736
See application file for complete search history.

(56) References Cited

U.S. PATENT DOCUMENTS

| | | | |
|---|---|---|---|
| 2002/0017144 A1* | 2/2002 | Miles | G01N 3/32 73/808 |
| 2003/0074976 A1* | 4/2003 | Ahmad | G01N 3/32 73/808 |
| 2011/0138926 A1* | 6/2011 | Bassot | G01N 3/56 73/826 |

OTHER PUBLICATIONS

Written Opinion of the International Searching Authority dated Jul. 3, 2014, issued in corresponding International Application No. PCT/FR2014/051124, filed May 15, 2014, 8 pages.
International Preliminary Report on Patentability dated Nov. 17, 2015, issued in corresponding International Application No. PCT/FR2014/051124, filed May 15, 2014, 1 page.

* cited by examiner

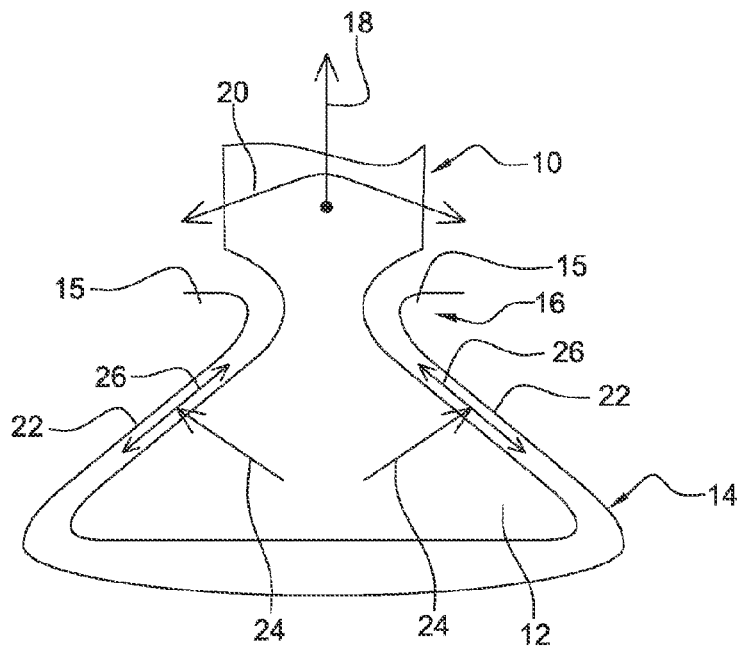
Fig. 1
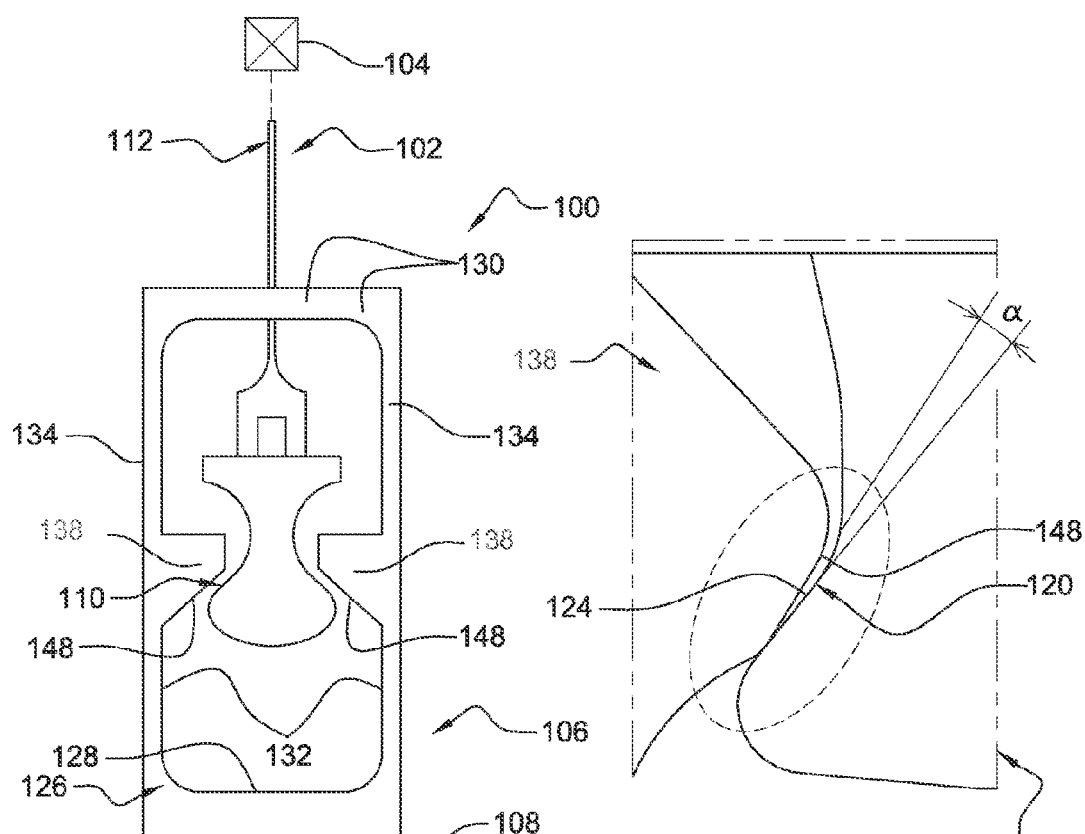
Fig. 2
Fig. 3

APPARATUS AND METHOD FOR OPTIMIZING A TEST BED THAT IS UTILIZED FOR TESTING LOW CYCLE AND HIGH-CYCLE FATIGUE INCLUDING MODIFYING A SUPPORT

TECHNICAL FIELD

The present invention relates to a method for optimising a low-cycle, and optionally combined low-cycle and high-cycle, fatigue test rig, for reproducing a support of turbine engine parts, such as a support of at least one blade root on a recess projection of a rotor disc, and the corresponding support member thereof.

PRIOR ART

A turbine-engine rotor disc comprises, on the periphery thereof, an annular array of recesses into which blade roots are fitted, which blade roots are for example of the dovetail type, to form a rotor wheel. In operation, the blades are subjected to centrifugal forces, and the roots thereof are supported by lateral projections of the recesses in the disc. The blades are further subjected to oscillations related to the aerodynamic forces which cause relative sliding between the blade roots and the disc. This loading affects the service life of the blade-disc attachments.

The analysis of the service life of the blade-disc attachments is based on calculations which are made complex by the effect of contact on the calculated stresses and service lives. The calculation for predicting service lives is possible by means of a complete digital model. The difficulty of the model put in place lies in the input data required. The model requires a correlation between a stress field seen under the blade-disc contact and the number of cycles for initiating a corresponding crack.

In view of this analysis, it is necessary to devise a test which is capable of reproducing, in laboratory conditions, blade-disc contact which is subjected to low-cycle fatigue (LCF) or low-cycle and high-cycle fatigue (HCF) loading. A test rig should make it possible to determine, by means of experiment, the service life of the blade-disc contact. These experimental data will subsequently be used to set the digital methodologies for determining service life on the actual parts for which it is impossible to determine a service life by means of experiment.

In the current art, low-cycle, and optionally high-cycle, fatigue test rigs each comprise a support member which is fixed to a mount and defines at least one bearing surface, and a test piece which is connected to traction means for loading the test piece so that it bears against the or each bearing surface of the member.

However, said test rigs are not completely satisfactory because they are designed without taking into account the features of the support member and the test piece, the quality of the contact between the support member and the test piece, the industrial application of the tested contact, the dynamic behaviour of the rig during a high-cycle fatigue test, etc.

The aim of the present invention is in particular to provide a simple, effective and economical solution to at least some of the above-mentioned problems.

SUMMARY OF THE INVENTION

The invention proposes a method for optimising a low-cycle, and optionally combined low-cycle and high-cycle, fatigue test rig, said test rig being intended to reproduce a support of turbine engine parts, such as a support of at least one blade root on a recess projection of a rotor disc, and comprising a support member which is fixed to a mount and defines at least two bearing surfaces, and a test piece which is connected to traction means for loading the test piece so that it bears against the or each bearing surface of the member, the method comprising the steps consisting in:
 determining variable, in particular geometrical, parameters of the support member and/or the test piece, as well as ranges of variation of said parameters,
 determining at least one objective to be achieved or optimised, a variation of the values of at least some of the above-mentioned parameters affecting the objective,
 modifying one or more of the values of the above-mentioned parameters, in the respective ranges thereof, and determining those which make it possible to achieve or optimise the objective so as to identify optimised parameters, and
 producing a support member and/or a test piece based on fixed parameters and parameters optimised for equipping a new rig, or modifying the support member and/or the test piece of an existing rig based on the optimised parameters.

The method is notable in that the support member further comprising two middle portions respectively supporting the two bearing surfaces, each middle portion being connected, on the side opposite the traction means, by a first arm to a base for fixing to the mount and, on the side of the traction means, by a pair of second arms to ends of two parallel crossbars which are at a distance from one another, the opposite ends of the bars being connected by another pair of second arms to the other middle portion, the method includes among the variable parameters at least one dimension of the second arms of each pair, and/or the angle of inclination of said second arms with respect to the corresponding crossbar or with respect to the bearing surface of the corresponding middle portion.

The invention thus proposes a method making it possible to optimise specific parameters of the support member and the test piece in order to improve in particular the representativeness of the test with respect to the industrial application, as well as the reliability of the objectives of said test. The variable parameters are preferably geometrical parameters but can be other types of parameters or not only geometrical parameters. The invention further makes it possible to modify a test rig so that it adapts to any type of support of turbine engine parts, and further has the advantage of being able to be applied to an existing rig from the prior art.

The method according to the invention can be implemented by a computer system comprising an optimisation software such as the software DesignXplorer marketed by the company Ansys.

The variable parameters can include at least one dimension of the first arms, such as the length and/or thickness thereof, and/or the angle of inclination of said arms with respect to the base or with respect to the bearing surface, and/or the rigidity of said arms, and/or the height or length between the base and the bearing surface.

The objective to be achieved can be the parallelism and the contact of the bearing surfaces between the test piece and the support member, and/or a maximum amplitude of sliding between said surfaces, and/or a substantially homogeneous contact pressure between said surfaces.

When the surfaces of the test piece and the support member bear against a substantially rectangular region, the contact pressure can be considered to be substantially homogeneous when the ratio between the contact pressure in the region of a lower edge of the region and that in the region of an upper edge of the region is equal to approximately one.

In the case in which the rig is used for low-cycle and high-cycle fatigue tests and comprises two I-shaped parts having a flexible middle portion, one of which connects the support member to the mount and the other of which connects one end of a vibrating blade to the traction means, the other end of the blade being connected to the test piece, the rig further comprising excitation means cooperating with the I-shaped part connected to the blade for making said blade vibrate during the tests, the objective to be achieved can be a target vibration frequency of the blade. In the case in which at least two objectives are determined, at least some of said objectives are ranked in order of importance. Thus, in the case in which several values of parameters make it possible to optimise said objectives, the parameters chosen may be those which allow the best optimisation of the most important objective.

In the case in which the method is used to optimise a test rig reproducing the support of at least one blade root against a recess projection of a rotor disc, the bearing surfaces of the test piece can represent recess projection bearing surfaces of a rotor disc, and the bearing surfaces of the support member represent bearing surfaces of a blade root.

The invention also relates to a support member comprising at least two bearing surfaces which are intended to cooperate with bearing surfaces of a test piece in a test rig to reproduce a support of turbine engine parts, such as a support of at least one blade root against a recess projection of a rotor disc, and carry out low-cycle, and optionally high-cycle, fatigue tests. Since the support member is intended to be fixed to a mount and the test piece has to be connected to traction means for loading the test piece so that it bears against each bearing surface of the support member, the support member is characterised in that it further comprises two middle portions respectively supporting the two bearing surfaces, each middle portion being connected, on the side opposite the traction means, by a first arm to a base for fixing to the mount and, on the side of the traction means, by a pair of second arms to ends of two parallel crossbars which are at a distance from one another, the opposite ends of the bars being connected by another pair of second arms to the other middle portion.

Advantageously, the first arms of the support member are substantially collinear to the shearing forces applied to the bearing surfaces and the second arms are substantially collinear to the normal forces applied to said surfaces. This allows decoupling of the normal and shearing stresses. To be more precise, the geometry of the member (which is collinear both with the normal forces and with the shearing forces) makes it possible, by means of the deformations of such a structure, to maintain perfect plane-to-plane contact regardless of the loading.

The present invention also relates to a low-cycle, and optionally high-cycle, fatigue test rig, characterised in that it comprises a support member as described above and in that it is optimised by the method as described above.

DESCRIPTION OF THE DRAWINGS

The invention will be better understood, and other details, features and advantages of the invention will become apparent upon reading the following description, given by way of non-limiting example and with reference to the accompanying drawings, in which:

FIG. 1 is a very schematic view of the attachment of a blade root in a recess of a rotor disc of a turbine engine, FIG. 2 is a partial schematic view of a low-cycle fatigue test rig and shows a test piece and a support member of said rig, FIG. 3 is a larger-scale view of part of FIG. 2 and shows the region of contact between the test piece and the support member.

DETAILED DESCRIPTION

Figure 4:
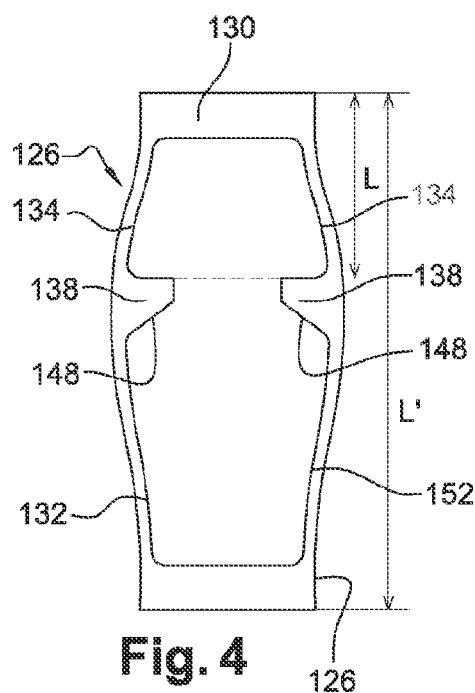
FIG. 4 is a schematic view of the support member from FIG. 2 during a fatigue test.

Reference is first made to FIG. 1, which schematically shows a blade-disc attachment of a turbine engine, the blade 10 comprising a root 12 which is engaged in a recess 14 in the periphery of a rotor disc 16, said disc comprising an annular array of recesses 14 of this type for receiving blade roots. The assembly formed by the disc 16 and the blades 10 form a rotor wheel of the turbine engine. In this case, the root 12 is of the dovetail type. Two adjacent recesses 14 in the disc 16 are separated from one another by a tooth 15, the teeth 15 located on either side of the root 12 of the blade from FIG. 1 being shown in part.

In operation, the blade 10 is subjected to centrifugal forces (arrow 18) and the vane thereof has a tendency to oscillate (arrow 20), causing the lateral portions of the blade root 12 to bear and slide against lateral projections 22 of the recess 14 in the disc. The arrows 24 show normal forces which are applied to the surfaces opposing the blade root 12 and the recess 14, and the arrows 26 denote shearing forces which are applied to said surfaces.

FIGS. 2 to 4 show a test rig which is designed to reproduce two blade-disc contacts which are subjected to low-cycle fatigue (LCF) loading, in order to determine, by means of experiment, the service life of said contacts.

The test rig 100 basically comprises two portions, a first portion 102 which is connected to traction means 104 and which is intended to reproduce a tooth of a rotor disc, and a second portion 106 which is connected to a fixed mount 108 and which is intended to reproduce portions of two blade roots cooperating with said tooth.

The first portion 102 comprises a test piece 110 which is fixed at the end of a blade 112, the other end of which is connected to the traction means 104. Said traction means 104 comprise for example an actuator, the free end of the rod of which is connected to the blade 112, and the cylinder of which is supported by a fixed portion of the test rig. Said actuator is preferably oriented in parallel with the blade 112 in such a way that the traction force is parallel to the longitudinal axis of the blade 112.

The test piece 110 comprises a portion which is shaped into a disc tooth, said portion reproducing portions of two adjacent recesses in the disc. Said portion has a dovetail general shape and comprises two lateral faces which are shaped to reproduce the projections 120 of two adjacent recesses in the disc. Each of said projections 120 comprises a relatively planar bearing surface 124 (FIG. 3).

The second portion 106 of the test rig 100 comprises a support member 126 comprising a base 128 which is fixed to the mount 108 and two crossbars 130 which are parallel to one another and to the base and are at a distance from one another, said bars 130 being connected to the base by arms 132, 134 which support bearing middle portions 138 of the test piece 110.

The base 128 has a parallelepiped shape and is preferably fixed in a flat manner in a horizontal position on the mount 108. Said base is connected by two opposite ends to lower ends of first arms 132, the upper ends of which are connected to middle portions 138 supporting bearing surfaces 148, said middle portions 138 being connected to the lower ends of second arms 134, the upper ends of which are connected to the ends of the crossbars 130. The bearing surfaces 148 are intended to cooperate with the bearing surfaces 124.

There are two first arms 132 or lower arms, each arm 132 connecting an end of the base 128 to a lower end of the middle portion 138. In the resting position, said arms 132 are substantially perpendicular to the base 126.

There are four second arms 134 or upper arms, each middle portion 138 being connected by a pair of second arms 134 to first ends of the crossbars 130, the opposite ends of which are connected by the other pair of second arms 134 to the other middle portion 138. The second arms 134 of each pair are parallel and at a distance from one another, each crossbar 130 and the second arms 134 which are connected to said bar being located substantially in the same plane. In the resting position, said arms 134 are substantially perpendicular to the bars 130.

In the assembled position shown in FIG. 2, the blade 112 passes between the bars 130 and the test piece 110 extends between the middle portions 138, in such a way that the surfaces 124 of the test piece 110 bear against the surfaces 148 of the middle portions 138.

As can be seen in FIG. 3, during a fatigue test, even if the bearing surfaces 124, 148 of the test piece 110 and of the support member 126 are perfectly parallel and bear against one another at the start of the test, it is possible, as a result of the deformations of the parts, for said surfaces to become misaligned and move away from one another, which leads to the appearance of an opening angle α in the contact region.

This drawback is eliminated as a result of the optimisation method according to the invention which makes it possible to modify the support member and/or the test piece so as to ensure that the opening angle α remains zero for the entire duration of the test.

As can be seen in FIG. 4, the parts of the test rig 100 and in particular the support member are subjected to forces and undergo deformations which can be seen here by deformations of the arms 132, 134 of the support member 126 which lead to the middle portions 138 and the bearing surfaces 148 moving away from one another and risk leading to the appearance of an opening angle α between said surfaces.

As explained above, the method according to the invention makes it possible to optimise one or more variable, in particular geometrical, parameters of the test rig in order to best achieve an objective. The desired objective in this case is to prevent the appearance of the opening angle α during a test; said angle must therefore remain zero. The variable geometrical parameter in this case is the position of the contact region which corresponds in FIG. 4 to the dimension L extending between the upper edges of the bars 130 and the lower ends of the arms 134 (and is substantially equal to the sum of the length of the arms 134 and the thickness of the bars 130, said dimensions being measured in a direction which is substantially parallel to the longitudinal axis of the above-mentioned blade 112).

The position of the contact region is expressed as a percentage of the total length L' of the support member 126. The position P of the contact region is thus equal to the ratio (L:L')*100.

Figure 5:
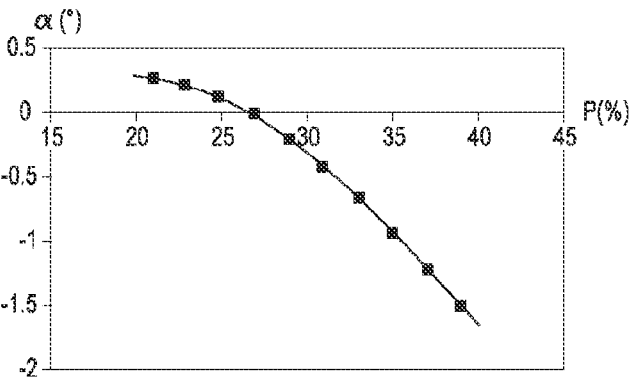
FIG. 5 is a graph showing the change in the opening angle in the contact region as a function of the position of said region.

The method according to the invention consists in particular in determining by calculation the effect of the variation in P on the opening angle α and in determining for which value of P the objective is achieved (α=0). The method can consist in creating a graph as shown in FIG. 5 in which the range of variation in P is [20%-40%]. It is noted that the angle α is zero for P=approximately 27%. The region of contact between the test piece 110 and the support member 126 of the test rig 110 from FIGS. 2 and 4 must thus be approximately 27% of the total length of the support member, measured from the crossbars 130.

Figure 6:
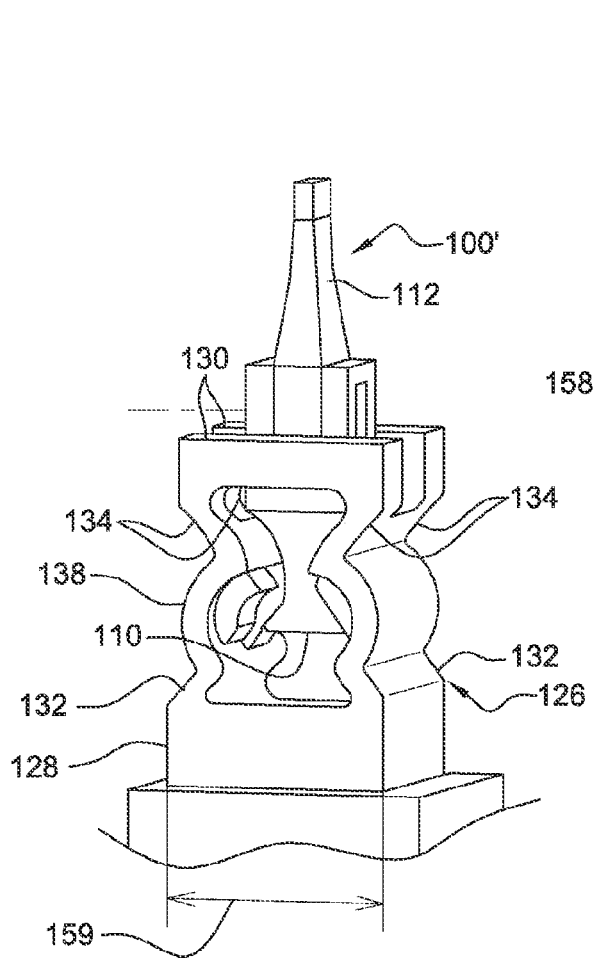
FIG. 6 is a partial schematic perspective view of another low-cycle fatigue test rig.
Figure 7:
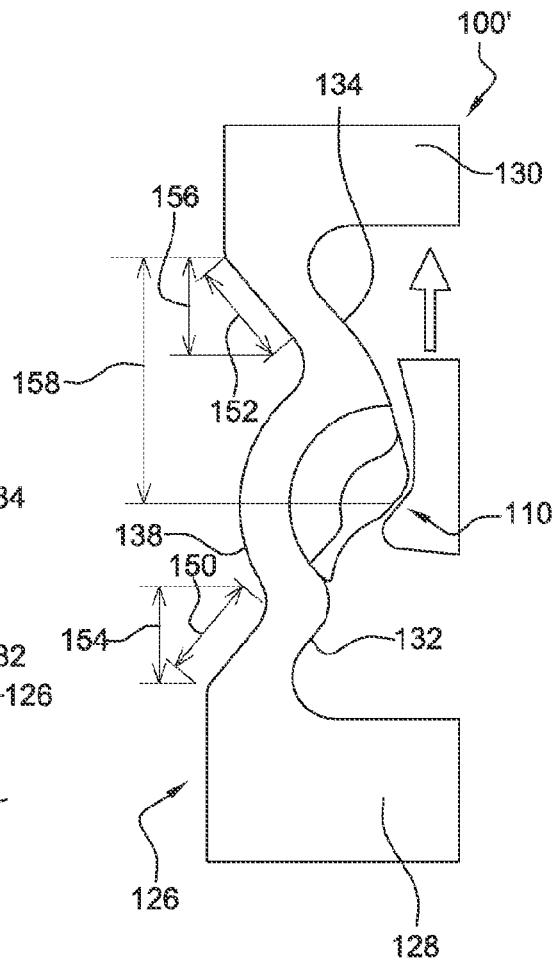
FIG. 7 is a half view of the support member and the test piece of the test rig from FIG. 6.

FIGS. 6 and 7 show another low-cycle fatigue (LCF) test rig 100' which has been designed and optimised by means of the method according to the invention.

Said test rig 100' differs from that 100 described above in particular in that the arms 132, 134 thereof are inclined with respect to the base 128 and to the crossbars 130, the upper ends of the arms 132 each being connected to the lower end of a middle portion 138 formed as a portion of a cylinder, the upper end of which is connected to the lower ends of the arms 134. The arms 132 are substantially collinear to the shearing forces applied to the surfaces 124, 148, and the arms 134 are substantially collinear to the normal forces applied to said surfaces.

The method according to the invention has been applied using the following parameters as variable geometrical parameters: the angle of inclination of each arm 132, 134 (with respect to the base 128 for example), the thickness of the different portions of the support member 126, and the rigidity and the length of the arms 132, 134. In FIGS. 6 and 7, the arrows denoted by reference numerals 150-159 show some of said parameters: arrows 150, 152 show the lengths of the arms 132, 134 respectively, arrows 154, 156 show the heights of said arms 132, 134 respectively, arrow 158 shows the height or position of the contact region, and arrow 159 shows the width of the base 128 or the support member 126.

Figure 8:
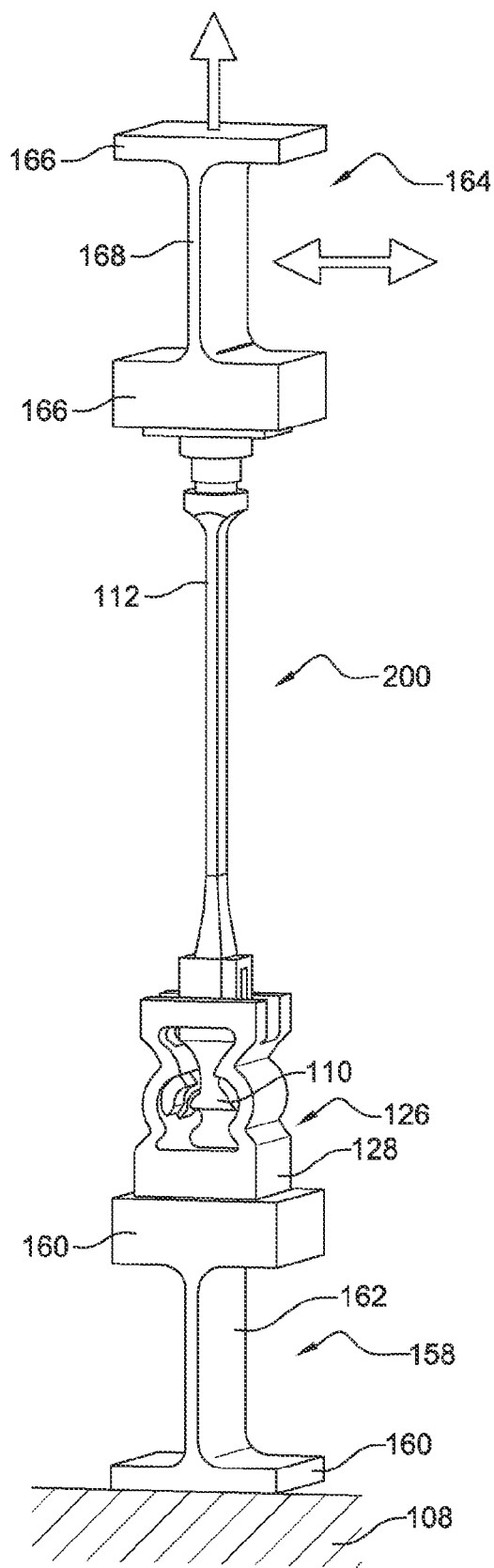
FIG. 8 is a schematic perspective view of a low-cycle and high-cycle fatigue test rig.

FIG. 8 shows a test rig 200 which is designed to reproduce two blade-disc contacts which are subjected to low-cycle fatigue (LCF) and high-cycle fatigue (HCF) loading.

The test rig 200 has all the above-mentioned features of the rig 100', and additionally the following features.

The member 126 is fixed to the mount by means of an I-shaped part 158. Said part 158 comprises two parallel, substantially parallelepipedal, solid blocks 160 which are interconnected by a flexible wall 162 which is perpendicular to the blocks. The base 128 of the member 126 is applied and fixed to one of the blocks 160, the second block being fixed to the mount 108.

The blade 112 is fixed to the traction means by means of another I-shaped part 164, which is substantially identical to the first 160. One of the blocks 166 of said part 164 is fixed to one end of the blade 112 (opposite the test piece 110) and the other block 166 is connected to the traction means. The flexible walls 162, 168 of the I-shaped parts are substantially coplanar.

The test rig 200 comprises high-frequency excitation means, such as a shaker, which bear against the I-shaped part 164 which is connected to the blade 112, for example in the region of the block 166 which is connected to said blade, for making the blade 112 vibrate.

Figure 9:
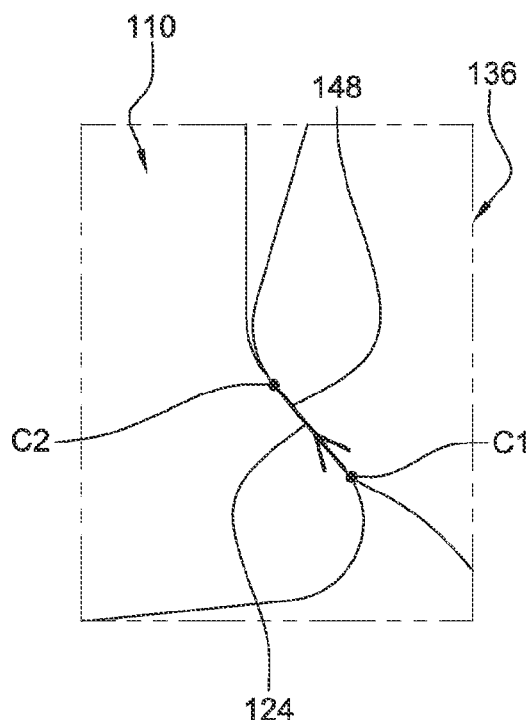
FIG. 9 is a larger-scale view of part of FIG. 8 and shows the region of contact between the test piece and the support member.
Figure 10:
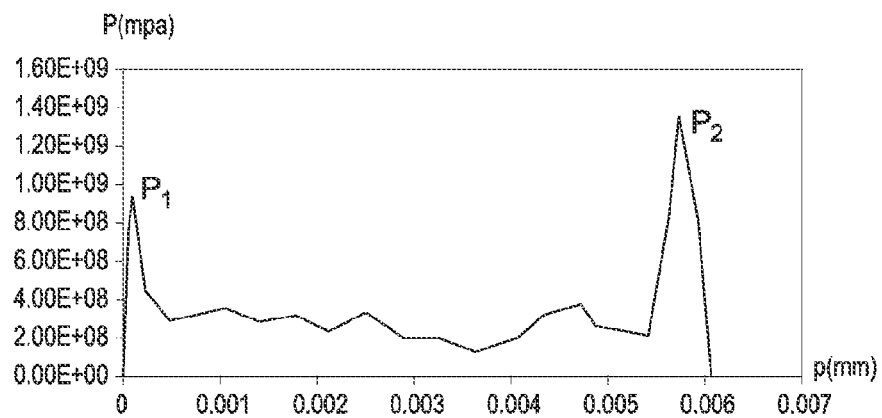
FIG. 10 is a graph showing the change in the contact pressure between the test piece and the support member, between an upper edge and a lower edge of the contact region.

FIG. 9 is a larger-scale view of the region of contact between the test piece 110 and the support member 126 from FIG. 8. During the fatigue test, it is important for the contact pressure between the bearing surfaces 124, 148 of the test piece 110 and the support member 126 to be substantially homogeneous over the entire extent of said surfaces. The contact region can be equated to a substantially rectangular and planar surface. The contact pressure is considered to be homogeneous when the contact pressure P1 located in the region of the lower edge (in C1) of the contact region is substantially equal to the contact pressure P2 located in the region of the upper edge (in C2) of the contact region, that is to say that the ratio P1:P2 is substantially equal to 1. The graph in FIG. 10 shows the change in the contact pressure P(mPa) as a function of the position in the contact region, measured in millimeters from C1, in one embodiment.

Figure 11:
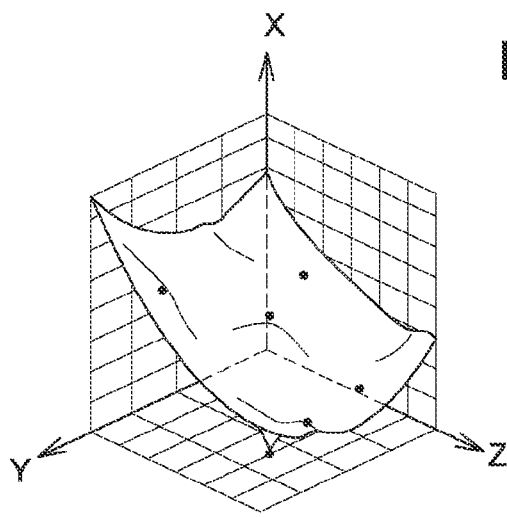
FIGS. 11 and 12 are graphs showing the effect of the variation of geometrical parameters of the support member on the homogeneity of the contact pressure between the test piece and the support member and on the amplitude of sliding therebetween.
Figure 12:
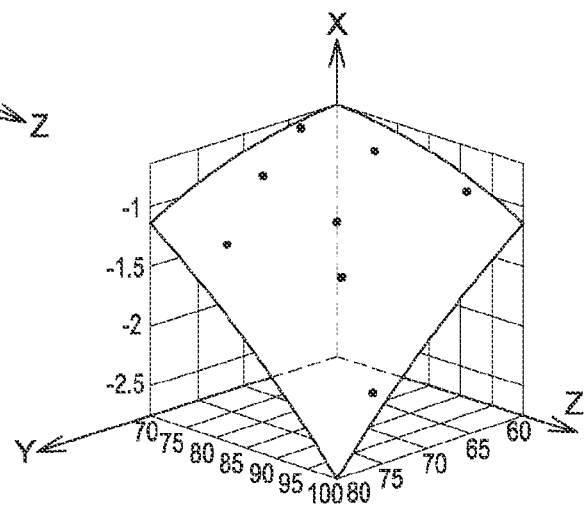

FIGS. 11 and 12 show one embodiment of the method according to the invention which is used in this case to achieve two objectives simultaneously: the first being the above-mentioned pressure ratio P1:P2 which must be equal to approximately 1, and the second being the amplitude of sliding of the bearing surfaces 124, 148, which must be the highest possible.

FIGS. 11 and 12 show the response surfaces of a series of calculations, that is to say the value of the optimisation criteria as a function of the variable input parameters. Said response surfaces consequently make it possible to propose the best candidate with respect to input criteria.

FIG. 11 shows the change in the pressure ratio (in X), as a function of the length of the arms 132 (arrow 154 in FIG. 7—in Y (mm)) and the length of the arms 134 (arrow 156 in FIG. 7—in Z (mm)). FIG. 12 shows the amplitude of sliding of the bearing surfaces 124, 148 (in X ($10^{-4}$ m), as a function of the length of the arms 132, 134 (in Y (mm) and Z (mm) respectively).

The table below includes the objectives of the optimisation steps of the method according to the invention.

|  | Length of the arms 132 (mm) | Length of the arms 134 (mm) | Amplitude of sliding (m) | Pressure ratio P1:P2 |
| --- | --- | --- | --- | --- |
| Objective |  |  | To be maximised | Target value sought |
| Target value |  |  |  | 1 |
| Importance |  |  |  | High |
| Candidate A | 99.951 | 79.953 | −0.00027375 | 0.83284 |
| Candidate B | 96.879 | 79.944 | −0.00025343 | 0.83521 |
| Candidate C | 81.903 | 79.918 | −0.00016705 | 0.99952 |

The range of variation in the length of the arms 132 is [80, 100] mm and that in the length of the arms 134 is [79, 80] mm. Each candidate A, B and C corresponds to a set of values of the parameters considered. As explained above, the objective in this case is both to maximise the amplitude of sliding of the bearing surfaces and to ensure that the pressure ratio P1:P2 is as close to 1 as possible. In the criteria of importance, it is noted that the pressure ratio objective takes precedence over the sliding amplitude objective.

It is noted that the candidates A and B make it possible to obtain a relatively high amplitude of sliding, and that the candidate C makes it possible to obtain a pressure ratio which is close to 1 together with a relatively good amplitude of sliding. Given the importance of the pressure ratio objective, the candidate C is chosen, that is to say that the corresponding values of the lengths of the arms 132, 134 are considered to be values which are optimised for achieving the above-mentioned double objective.

In the case in which the objective to be achieved is a vibration frequency, it is necessary to adapt the rig so as to be able to apply said frequency because the excitation or HCF loading frequency is not constant. The HCF loading is primarily controlled by the geometry and the rigidity of the support member 126 and above all by the geometry and the rigidity of the blade 112. The vibration frequency is not controlled and depends for example on the geometry and the rigidity of the support member 126 and the blade 112.

Figure 13:
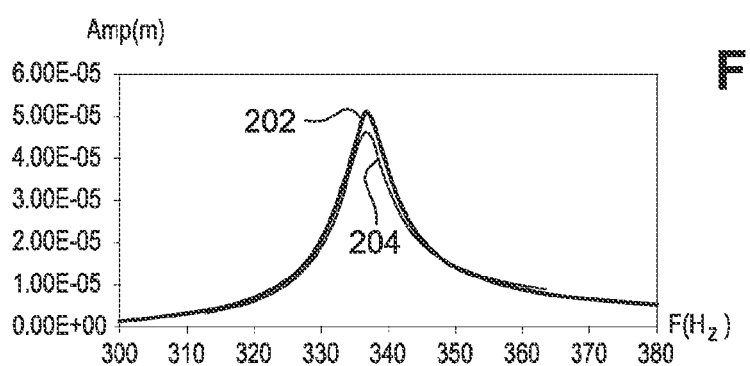
FIG. 13 is a graph showing the change in the amplitude of displacement of the contact region as a function of the vibration frequency of a blade of the test rig.

The optimisation method is applied with the same procedure as previously, thus proposing modifications of parameters of the test rig. The entire frequency behaviour of the new rig is then calculated and superimposed on the target response. FIG. 13 is a graph showing the change in the amplitude of displacement (Amp (m)) of the bearing surfaces 124, 148 of the test piece 110 and the bearing member 126 as a function of the vibration frequency of the blade 112. The curve 202 shows the target frequency response and the curve 204 shows the frequency response calculated by the method according to the invention. It is noted that the method for optimising the rig is effective and that the technology of the test rig makes it possible, by varying the parameters, to adapt the frequency response depending on the application.

The method according to the invention can be implemented by a computer system which is intended in particular to carry out the optimisation calculations.

The last step of the method according to the invention consists in producing a support member and/or a test piece based on fixed parameters and parameters optimised for equipping a new rig, or in modifying the support member and/or the test piece of an existing rig based on the optimised parameters.

The invention claimed is:

1. Method for producing an optimized low-cycle, and/or high-cycle, fatigue test rig, said test rig representative of a support of turbine engine parts, including a support of at least one blade root on a recess projection of a rotor disc, and comprising a support member which is fixed to a mount and defines at least two bearing surfaces, the test rig further comprising a test piece which is connected to a traction means for loading the test piece so that it bears against one or more of the at least two bearing surfaces of the support member, the method comprising the steps of: selecting variable, geometrical, parameters of the support member and/or the test piece, and selecting ranges of variation of values of said variable parameters;

selecting at least one design objective of the test rig to be achieved or optimized, the variation of the values of at least one of said variable parameters affecting the design objective; wherein the design objective to be achieved is selected from the group consisting of the parallelism and the contact of the bearing surfaces between the test piece and the support member, a maximum amplitude of sliding between said surfaces, a homogeneous contact pressure between said surfaces, and combinations thereof;

testing one or more of the values of said variable parameters, in the respective ranges thereof, and determining those values which make it possible to achieve or optimize the design objective so as to identify optimized parameters; and producing a support member and/or a test piece based on fixed parameters and the optimized parameters or equipping a new test rig, or modifying the support member and/or the test piece of an existing test rig based on the optimized parameters, wherein the support member extends along a longitudinal direction and further comprises two middle portions respectively supporting the two bearing surfaces, each middle portion being connected, on the side opposite the traction means, by a first arm to a base for fixing to the mount and, on the side of the traction means, by a pair of second arms to first ends of two parallel crossbars which are at a distance from one another, the opposite second ends of the crossbars being connected by another pair of second arms to the other middle portion, the two pairs of second arms and the first arms extending along the longitudinal direction and in opposite direction with regard to the middle portion; and wherein said variable parameters include at least one dimension of the second arms of each pair, and/or the angle of inclination of said second arms with respect to the corresponding crossbar or with respect to the bearing surface of the corresponding middle portion.

2. Method according to claim 1, wherein the variable parameters include at least one dimension of each first arm, and/or the angle of inclination of each first arm with respect to the base or with respect to the bearing surface of the corresponding middle portion, and/or the height or length between the base and the bearing surfaces.

3. Method according to claim 1, wherein the design objective to be achieved is the parallelism and the contact of the bearing surfaces between the test piece and the support member.

4. Method according to claim 1, wherein the test rig being used for low-cycle and high-cycle fatigue tests and comprising two I-shaped parts having a flexible middle portion, one of which connects the support member to the mount and the other of which connects one end of a vibrating blade to the traction means, the other end of the blade being connected to the test piece, the rig further comprising excitation means cooperating with the I-shaped part connected to the blade for making said blade vibrate during the tests, the design objective to be achieved is a target vibration frequency of the blade.

5. Method according to claim 1, wherein in the case in which at least two design objectives are determined, at least some of said design objectives are ranked in order of importance.

6. Method according to claim 1 wherein the test rig represents the support of at least one blade root against a recess projection of a rotor disc, and wherein the bearing surfaces of the test piece represent recess projection bearing surfaces of a rotor disc, and the bearing surfaces of the support member represent bearing surfaces of a blade root.

7. Low-cycle, and/or high-cycle, fatigue test rig, comprising:

a support member including at least two bearing surfaces for cooperating with bearing surfaces of a test piece in a test rig to represent a support of turbine engine parts, including a support of at least one blade root against a recess projection of a rotor disc, and to carry out low-cycle and/or high-cycle, fatigue tests, the support member configured to be fixed to a mount, and the test piece having to be connected to traction means for loading the test piece so that it bears against each bearing surface of the support member, wherein the support member further comprises two middle portions respectively supporting the two bearing surfaces, each middle portion being connected, on the side opposite the traction means, by a first arm to a base for fixing to the mount and, on the side of the traction means, by a pair of second arms to ends of two parallel crossbars which are at a distance from one another, the opposite ends of the bars being connected by another pair of second arms to the other middle portion wherein the support member is optimized by the method according to claim 1.

8. Method according to claim 1, wherein the design objective to be achieved is a maximum amplitude of sliding between said surfaces.

9. Method according to claim 1, wherein the design objective to be achieved is a homogeneous contact pressure between said surfaces.

10. Method according to claim 9, wherein the surfaces of the test piece and the support member bearing against a rectangular region, the contact pressure is considered to be homogeneous when the ratio between the contact pressure in the region of a lower edge of the region and that in the region of an upper edge of the region is equal to approximately one.

11. Method according to claim 1, wherein the surfaces of the test piece and the support member bearing against a rectangular region, the contact pressure is considered to be homogeneous when the ratio between the contact pressure in the region of a lower edge of the region and that in the region of an upper edge of the region is equal to approximately one.

12. Support member comprising at least two bearing surfaces for cooperating with bearing surfaces of a test piece in a test rig to represent a support of turbine engine parts, including a support of at least one blade root against a recess projection of a rotor disc, and to carry out low-cycle, and/or high-cycle, fatigue tests, the support member configured to be fixed to a mount, and the test piece having to be connected to traction means for loading the test piece so that it bears against each bearing surface of the support member, wherein the support member extends along a longitudinal direction and further comprises two middle portions respectively supporting the two bearing surfaces, each middle portion being connected, on the side opposite the traction means, by a first arm to a base for fixing to the mount and, on the side of the traction means, by a pair of second arms to first ends of two parallel crossbars which are at a distance from one another, the opposite second ends of the bars being connected by another pair of second arms to the other middle portion, the two pairs of second arms and the first arms extending along the longitudinal direction and in opposite direction with regard to the middles portion.

13. Support member according to claim 12, wherein the first arms of which are collinear to the shearing forces applied to the bearing surfaces and the second arms are collinear to the normal forces applied to said surfaces.

* * * * *